United States Patent [19]

Steuernagel et al.

[11] 4,191,703

[45] Mar. 4, 1980

[54] PROCESS FOR THE MANUFACTURE OF SULFURIC ACID SEMI-ESTER COMPOUNDS

[75] Inventors: Hans H. Steuernagel, Kelkheim; Ernst Hoyer, Frankfurt am Main, both of Fed. Rep. of Germany

[73] Assignee: Hoechst Aktiengesellschaft, Frankfurt, Fed. Rep. of Germany

[21] Appl. No.: 913,538

[22] Filed: Jun. 8, 1978

Related U.S. Application Data

[63] Continuation of Ser. No. 820,848, Aug. 1, 1977, abandoned.

[30] Foreign Application Priority Data

Aug. 3, 1976 [DE] Fed. Rep. of Germany ....... 2634787

[51] Int. Cl.$^2$ ........................................... C07C 141/18
[52] U.S. Cl. .................. 260/458 C; 260/147; 260/148; 260/149; 260/151; 548/221
[58] Field of Search .......... 260/458 C, 307 D, 307 C, 260/151, 147, 148, 149

[56] References Cited

U.S. PATENT DOCUMENTS

| | | | |
|---|---|---|---|
| 3,135,730 | 6/1964 | Heyna et al. ............... | 260/149 X |
| 3,135,779 | 6/1964 | Hoyer et al. ............... | 260/458 C |
| 3,414,579 | 12/1968 | Remy ............................ | 260/151 X |
| 3,462,409 | 8/1969 | Meininger et al. ........ | 260/147 |

FOREIGN PATENT DOCUMENTS

1153029  8/1963  Fed. Rep. of Germany ............ 260/147

*Primary Examiner*—Charles F. Warren
*Attorney, Agent, or Firm*—Curtis, Morris & Safford

[57] ABSTRACT

An improved and novel process has been found for the esterification of amino-benzoxazolone compounds containing a β-hydroxyethylsulfonyl group, by means of sulfuric acid or sulfur trioxide, with simultaneous or subsequent hydrolytic cleavage of the oxazolone ring, wherein the esterification and optional hydrolytic ring cleavage are performed in a machine which is operating with a kneading action and effect, using per mol of β-hydroxyethylsulfonyl compound 1 to 20 times the equivalent molar amount of concentrated sulfuric acid, oleum or sulfur trioxide. This novel process has the great advantage that great amounts of sulfuric acid are saved which would contaminate the waste-water, also in form of sodium sulfate formed after the required neutralization. Furthermore, the β-sulfatoethylsulfonyl compounds formed as end-products in the esterification process are obtained in higher yields, in a higher esterification rate and in a higher purity. They may be obtained in form of a powder or plastic mass, which is conveniently transportable and storable, and can advantageously be used, if ring cleavage had taken place, without intermediate isolation of the pure sulfato compound itself, directly for the preparation of azo dyestuffs which are low in content of inert salts and possess a high tinctorial strength and purity.

5 Claims, No Drawings

PROCESS FOR THE MANUFACTURE OF SULFURIC ACID SEMI-ESTER COMPOUNDS

This is a continuation of application Ser. No. 820,848, filed Aug. 1, 1977, and now abandoned.

The present invention relates to an improved process for the manufacture of compounds of the formula

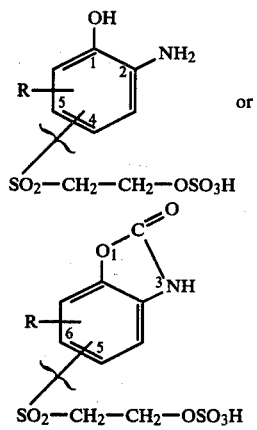

by the esterification and optionally hydrolytic ring cleavage, starting from a compound of the formula

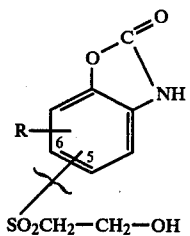

which is characterized in that the reaction is carried out with 1 to 2 times the equimolar amount, relative to moles of SO$_3$, of 92 to 100% strength sulfuric acid or of sulfur trioxide or of sulfuric acid containing sulfur trioxide, optionally with the subsequent addition of water, while mixing thoroughly.

In these formulae (I), (II) and (III), R represents hydrogen or a lower alkyl group, such as a methyl or ethyl group and of these, in particular, the methyl group, or the nitro group or a chlorine or bromine atom; the β-hydroxy- or β-sulfatoethylsulfonyl group is in the 5-position or 6-position of the benzoxazolone ring or in the 4-position or 5-position of the benzene nucleus of the aminophenol.

The manufacture of 2-amino-phenol-4-β-sulfatoethyl sulfone and -5-β-sulfatoethyl sulfone and of 5-β-sulfatoethyl sulfonyl- and 6-β-sulfatoethylsulfonyl-benzoxazolone by the process according to the invention is particularly preferred.

The compounds of the formula (II) and (III) are suitable for use as precursors (diazo components) for the manufacture of azo dyestuffs.

The conversion of compounds of the formula (I) into compounds of the formula (II) with hydrolytic cleavage of the oxazolone ring is in itself known. However, the method described hitherto requires large excesses of sulfuric acid which, either during the working up of the esterification product of the formula (II) and during its isolation or during its further processing to a dyestuff, must be diluted with water, neutralized and separated off from the esterification product or from the dyestuff. Thus recovery of the sulfuric acid is virtually excluded. In addition, the acids, as such or in the neutralized form as soluble sulfates, pollute the effluent.

Furthermore, the known esterification process has the disadvantage that the compounds of the formula (II) are obtained as solutions in sulfuric acid. These solutions are not very suitable for storage, for example for further processing carried out later.

Thus, according to German Pat. No. 1,153,029, the esterification of a compound of the formula (I) is carried out with 6 times the equimolar amount of concentrated sulfuric acid. After diluting the sulfuric acid solution with a large amount of ice and water, the compound of the formula (II) obtained is isolated as a solid by suction (filtering off). In this procedure, it is obtained in a yield of only 67% of theory; the rest remains in the mother liquor, as does the excess dilute sulfuric acid which must be neutralized for the effluent. However, the product which cannot be isolated and the sodium sulfate considerably pollute the effluent.

Neutralization of the excess sulfuric acid with calcium carbonate and filtering off of the sparingly soluble calcium sulfate, such as is described in Example 2 of German Pat. No. 1,153,029, indeed eliminates pollution of the effluent, but requires additional expenditure on labor and material; furthermore, this method has the disadvantage that the gypsum thus obtained must be dumped as unusable industrial waste.

Likewise, the pollution of the effluent is very high when aminophenol manufactured by the known process is used directly, after dilution with ice and water, for the manufacture of an azo dyestuff (diazotization and coupling with the desired coupling component and, if appropriate, metallization): the dyestuff manufactured is isolated by salting out with sodium chloride or potassium chloride, while the sulfate and a large proportion of the chlorides remain dissolved. However, an effluent-free isolation of the dyestuffs by evaporating or spray-drying the dyestuff solutions obtained, without previously separating off the sulfate, would lead to dyestuff powders which are very weak in color and contain a high proportion of neutral salts and which would scarcely be of interest for industrial use.

There was thus an urgent need for an esterification process which avoids these disadvantages and results in virtually no pollution of the environment or substantially less pollution of the environment.

An improved process has now been found for the esterification of the abovementioned compounds of the formula (I) to give their sulfuric acid semi-esters of the formulae (II) and (III), which is characterized in that the reaction of a compound of the formula (I) is carried out with 1 to 2 times the equimolar amount, relative to moles of SO$_3$, of 92 to 100% strength sulfuric acid or sulfur trioxide or sulfuric acid containing sulfur trioxide, preferably with a content of up to about 70, in particular from 15 to 65, % by weight of sulfur trioxide, while thoroughly mixing vigorously, preferably in a machine operating with a kneading action and effect, hereinafter called a kneader.

The reaction temperature can be between +10° C. and 180° C. As a rule, the temperature is regulated by means of the cooling or heating jacket of the reaction vessel or the kneader. Depending on the temperature and the mixing or kneading intensity as well as the esterifying agent employed, the treatment time of the reaction mixture in the kneader or mixing apparatus can be a few minutes to several hours.

The process can be carried out in a simple manner by either initially introducing one of the reactants into the reaction vessel provided with an intensively operating mixing device or into the machine operating with a kneading action and gradually adding the second component to this, or by adding both components simultaneously or as a mixture to this reaction vessel or the kneader.

Purely to esterify the compound of the formula (I) to give the compound of the formula (III), oleum or sulfur trioxide itself are preferably used as the esterifying agents; however, the esterification can also be carried out with 92 to 100% strength sulfuric acid at temperatures below 100° C., appropriately at 10° to 90° C. The reaction and kneading time is about 5 minutes to 6 hours.

The esterification of the compound of the formula (I) with simultaneous hydrolytic cleavage of the oxazolone ring is appropriately effected by carrying out the esterification by means of 92 to 100% strength sulfuric acid at a temperature from 100°–180° C., preferably at a temperature from 120°–160° C. The reaction is particularly advantageously carried out at a temperature between 120° and 160° C. in the course of a reaction and mixing, respectively kneading time of 2 to 20 hours, which under these conditions, depends in particular on the mixing, respectively kneading intensity applied, which in turn can depend on the type of machine.

A modification to this process for the manufacture of compound (II) from compound (I) consists in first esterifying the compound of the formula (I) in the manner indicated above and subsequently, if the esterification had been carried out with 92 to 100% strength sulfuric acid below 100° C., increasing the reaction temperature in the mixer or in the kneader to 100° to 180° C. for the hydrolytic cleavage or, if oleum or sulfur trioxide is used as the esterifying agent, carrying out the hydrolytic ring cleavage in the mixer or the kneader at 100° to 180° C. by slowly adding water in an amount such that a 92 to 100% strength sulfuric acid is obtained. The sulfuric acid used in the reactions with the compounds of the formula (I) is preferably employed as the 95–98% strength sulfuric acid, as so-called monohydrate (100% strength sulfuric acid) or as oleum. 1.0 to 1.5 times, in particular 1.1 to 1.5 times, the equimolar amount, relative to moles of $SO_3$, of esterifying agent are preferably used.

In order to improve the kneading action or the heat transfer in the kneading mixture during the kneading process, added inert adjuvants, such as kieselguhr, talc or metal powder, can also be co-processed and can then be separated off again from the sulfuric acid semi-ester prepared of the formula (III) or (II), or from a dyestuff manufactured from this, by simple filtration from an aqueous solution during the working up or further processing of the kneaded material.

By machines which operate with a kneading action there are to be understood those which are suitable for mixing, dispersing or homogenizing and which can process the liquid/solid components with one another, using high forces. In these machines, the processing (kneading) takes place under high pressure in the customary manner in such a way that parts of the machine running in the same direction or in opposite directions, preferably at different speeds, such as cylinders, discs, rollers, closely meshing toothed wheels and screws, mix the components with one another under high pressure, if appropriate with the application of shearing forces. Such machines having a kneading action, hereinafter called kneaders, are, in addition to actual kneaders and extruders themselves, also, for example, saw-toothed stirrers (dissolvers), rotor-stator mills, dispersers and roll mills. These machines can operate discontinuously and also continuously; a large number of them are known as being commercially available. Discontinuously operating kneaders are, for example, twin-bowl kneaders, such as sigma blade kneaders, dispersion kneaders and dispersion ram kneaders, and continuously operating kneaders are, for example, kneading extruders (for this, see also Ullmanns Encyclopädie der Technischen Chemie, volume 1 (1951), pages 725–727; and Ullmanns Encyclopädie der Technischen Chemie, 4th edition, volume 2 (1972), pages 23 and 292–299).

The reaction-mix (kneading product), both of the formula (II) and of the formula (III) is worked up, after the esterification and, if appropriate, hydrolytic ring cleavage, in the reaction vessel (kneader), in a manner which is customary and familiar to the expert. It is advantageously effected by dissolving the reaction mix in water, while simultaneously neutralizing the solution. The neutralization is preferably carried out with sodium bicarbonate or sodium carbonate. The neutral or very weakly acid solution is then evaporated to dryness or spray-dried, if appropriate after separating off the abovementioned inert adjuvants, for example by filtering or centrifuging. In this manner, for example in the case of neutralization with the abovementioned sodium salts, the compound of the formula (II) or (III) is obtained in the form of its sodium salt. Potassium bicarbonate or potassium carbonate can correspondingly be used for the neutralization. A further possibility for working up the reaction mix (kneaded mix) is to neutralize with calcium carbonate, after dissolving in water, to filter off the calcium sulfate which has formed and precipitated and to add sodium oxalate or oxalic acid and sodium carbonate or bicarbonate to the filtrate, to separate the solution in the customary manner from the precipitate formed, for example by filtering or centrifuging, and then to spray-dry it. In this new esterification process substantially lower amounts of gypsum are obtained than in the processes known hitherto.

An outstanding and important advantage of the esterification process, according to the invention, for the preparation of the aminophenol compounds of the formula (II) is, however, that working up of the end product is not necessary at all. In fact the reaction products leave the kneaders in the form of powders or crumbly or small lumps or as a plastic composition; they can be easily stored and transported in this form. Using them, an easy, effluent-free and non-polluting further processing is possible to give fibre-reactive azo dyestuffs of the formula (IV)

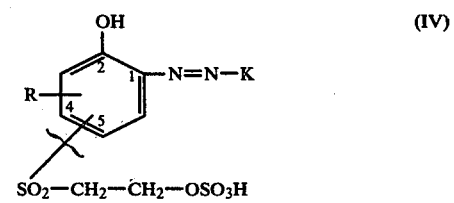

(IV)

in which R has the abovementioned meaning, the β-sulfatoethylsulfonyl group is in the 4-position or 5-position of the diazo component and K represents the radical of a coupling component which can also contain an azo grouping, in particular to give metal complex compounds of these dyestuffs, since the process products of the formula (II) resulting from the esterification process according to the invention are obtained with a degree of esterification of 95-100% and in high yield but, surprisingly, in addition also in a higher quality than from known processes. Accordingly, the metal complex dyestuffs obtainable from the process products of the esterification process according to the invention are of excellent quality, the shades of the dyeings and prints produced with them on cellulose fiber materials are of high purity, and in addition they are obtained in high yield, calculated relative to the starting compound of the above formula (I).

Below 50° C., the kneaded mix is usually obtained as a powder when 1 to 1.5 moles of esterifying agent are employed per mole of compound of the formula (I), and as a powder or in the plastic form when 1.5 to 2 moles of esterifying agent are used per mole of compound of the formula (I). The kneaded mix obtained according to the process can be stored and transported, preferably in the form of a powder, without problem in drums, so that further processing, for example to give dyestuffs, can be carried out at a time and place independent of the esterification.

In further processing to give azo dyestuffs, the kneaded mix is diazotized in an aqueous solution which is acid to Congo Red, it optionally being possible, depending on the amount of esterifying agent employed in the esterification process, to dispense, partially or completely, with a further addition of acid. The diazotization is carried out in a known and customary manner, as is also the subsequent coupling with a coupling component of the formula H-K, in which K has the abovementioned meaning, after adjusting the pH to an appropriate value, with the formation of a dyestuff of the abovementioned formula (IV), which in turn can be converted in an advantageous manner into a metal complex compound, in particular a copper, cobalt or chromium complex dyestuff, in the same reaction medium using a metal-donating agent.

Because of the relatively low content of sulfate, arising from the esterification, in the dyestuff solution thus manufactured, it is not necessary to separate out the dyestuffs by salting out with sodium chloride or potassium chloride and then to filter them off, but the weakly acid to neutral dyestuff solutions can, in an advantageous manner, be evaporated to dryness directly or subjected to spray-drying directly.

Dyestuff powders of high tinctorial strength which correspond, in their properties, to the products manufactured in a known manner, but which in general surpass these with respect to the degree of esterification of the β-hydroxyethylsulfonyl group, the content of dyestuff of the formula (IV) or its metal complex compound, the tinctorial strength, the solubility in water and the dyestuff yield, are thus obtained in very good yield and in excellent quality and purity.

Because of the good solubility of the dyestuff, the dyestuff solutions obtained can be employed directly for dyeing purposes, if appropriate after additionally concentrating to a smaller volume.

The present invention thus also relates to the simplified manufacture of fiber-reactive azo dyestuffs using the process products of the formula (II), obtained in the esterification process according to the invention, which is characterized in that the reaction mix (kneaded mix) is employed directly, without prior isolation of the compound of formula (II), as the diazo component, if appropriate dissolved in water, and diazotized in accordance with customary processes. The diazotization product is coupled with a coupling component, after adjusting the pH to a value appropriate for azo coupling, and the azo dyestuff thus obtained is optionally metallized, without prior isolation, and then isolated by spray-drying or evaporating.

The examples which follow serve to illustrate the subject of the invention. The parts by weight given in them bear the same relationship to parts by volume as the kilogram to the liter.

EXAMPLE 1

(a) 3,866 parts by weight of 6-(β-hydroxyethylsulfonyl)-benzoxazolone (94.4% pure) (i.e. a product containing 94.4% of the pure oxazolone compound, the residual portion being an electrolyte, such as sodium chloride or sodium sulfate) were initially introduced as a dry powder into a commercially available dispersion kneader (for example from Messrs. Werner & Pfleiderer, Stuttgart-Feuerbach), one kneading arm of which ran at a speed of 29 rpm and the other kneading arm of which ran at 21 rpm, and were heated to 110°-120° C. by means of jacket heating. 1,900 parts by weight of 98% strength sulfuric acid were then allowed to run during a period of 10 minutes, while the machine was running, and the reaction mixture was worked in the running kneader for about 14 hours at 140°-150° C. An initial foam formation was suppressed by adding a small amount of a commercially available silicone anti-foaming agent dropwise. A dark, pasty composition was formed, which on cooling to room temperature first became putty-like and then crystalline and finally gave a greenish-tinged grey powder. The kneader was then emptied. 4,960 parts by weight of 2-amino-1-hydroxy-5-(β-sulfatoethylsulfonyl)-benzene (86% pure), corresponding to a theoretical yield of 95.7%, were obtained as a powder.

(b) 2.0 parts by weight of the kneaded mix were stirred, at 0° to 5° C., into a mixture of 8 parts by volume of water and 2 parts by weight of ice, whilst simultaneously adding about 0.7 part by weight of sodium bicarbonate in portions. The pH value of the aqueous solution thus obtained was about 4.5; the solution was clarified by filtration and evaporated to dryness in vacuo at 60° to 65° C. After grinding, 2.1 parts by weight of a yellowish white powder were obtained which contained, in addition to 9% by weight of sodium sulfate, the pure compound of the formula

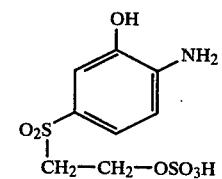

in the form of its sodium salt.

EXAMPLE 2

3,866 parts by weight of 6-(β-hydroxyethylsulfonyl)-benzoxazolone (94.4% pure) were initially introduced as a dry powder into a commercially available dispersion kneader. 1,607 parts by weight of 65% strength oleum were allowed to run in during a period of 20 minutes, while the machine was running. The temperature was kept below 100° C. by jacket cooling. After 2 hours, the putty-like reaction composition, which essentially contained the compound of the formula

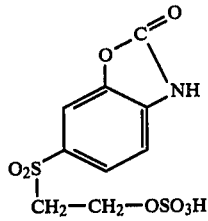

was heated up to 125°–130° C. by steam jacket heating. 250 parts by weight of water were added dropwise in the course of 2 hours; foam formation was suppressed by a silicone anti-foaming agent. After the water had been added, the reaction temperature was increased to 145°–155° C. and the composition was left in the running machine at this temperature for 20 hours. Thereafter, the contents of the kneader were cooled to room temperature, whereupon they became solid and turned into a powder. 5,100 parts by weight of 2-amino-1-hydroxy-5-($\beta$-sulfatoethylsulfonyl)-benzene (81% pure) were obtained; the degree of esterification was 96%.

EXAMPLES 3–7

If the process is carried out in an analogous manner to that described in Example 1 or 2, the starting compounds indicated in the tabular Examples 3 to 7 which follow give the corresponding sulfuric acid semi-esters of the formulae indicated (end products) therein in high purity and with a high degree of esterification and in high yield. These sulfuric acid semi-ester compounds can be excellently reacted in a known manner, for example in a manner analogous to that described in Examples 8 to 18 which follow, for the preparation of fiber-reactive azo dyestuffs and their metal complex compounds.

| Example | Starting compound | End product |
|---|---|---|
| 3 | (structure with CH₂-O₂S-CH₂-CH₂-OH substituent and CH₃, fused oxazolinone) | (structure with OH, NH₂, CH₂-O₂S-CH₂-OSO₃H, CH₃) |
| 4 | (structure with CH₂-O₂S-CH₂-CH₂-OH substituent and Cl, fused oxazolinone) | (structure with OH, NH₂, CH₂-O₂S-CH₂-OSO₃H, Cl) |
| 5 | (structure with Br and SO₂-CH₂-CH₂-OH, fused oxazolinone) | (structure with Br, OH, NH₂, SO₂-CH₂-CH₂-OSO₃H) |
| 6 | (structure with SO₂-CH₂-CH₂-OH, fused oxazolinone) | (structure with OH, NH₂, SO₂-CH₂-CH₂-OSO₃H) |

| Example | Starting compound | End product |
|---|---|---|
| 7 | (structure: O₂N-phenyl with fused O-C(=O)-NH ring, SO₂—CH₂—CH₂—OH) | (structure: O₂N, OH, NH₂ substituted phenyl, SO₂—CH₂—CH₂—OSO₃H) |

EXAMPLE 8

69 parts by weight of the kneaded mix manufactured under Example 1a were dissolved in a mixture of 300 parts by volume of water and 150 parts by weight of ice and diazotized with 40.1 parts by volume of 5 N sodium nitrite solution. After the diazotization reaction, a slight nitrite excess was destroyed after subsequently stirring for 15 minutes with a little amidosulfonic acid. The yellow diazonium salt solution was added to a solution, adjusted to neutral, of 76 parts by weight of 1-amino-8-hydroxy-4,6-disulfonic acid (84% strength) in 300 parts by volume of water. The pH was adjusted to 6 to 7 with anhydrous sodium carbonate and kept at this value until the coupling had ended (no further diazonium salt could be detected). 50 parts by weight of crystalline copper sulfate were then added and the pH value was adjusted to 4.5 to 5.0 with 50 parts by weight of crystalline sodium acetate and with sodium carbonate. The reaction solution was subsequently stirred at room temperature for 1 hour, then clarified, with the addition of 10 parts by weight of kieselguhr, and evaporated at 50° to 60° C.

The residue was ground; 240 parts by weight of a blue-black dyestuff powder were obtained, which contained 63% by weight of the dyestuff of the formula

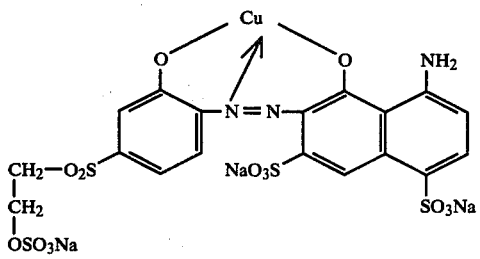

in the presence of an agent having an alkaline action, this dyestuff gave deep, navy blue dyeings and prints of very good fastness to light and wet processing on cotton and other cellulose fiber materials by the known customary dyeing procedures for reactive dyestuffs.

A dyestuff powder of the same dyestuff content and of equally good quality is obtained when the clarified dyestuff solution obtained during the manufacture is spray-dried instead of evaporated.

EXAMPLE 9

70 parts by weight of the kneaded mix, manufactured analogously to Example 1a, of the compound from Example 2 were dissolved and diazotized as described in Example 8. The solution of the diazonium salt was coupled with 136.5 parts by weight of 1-acetylamino-8-hydroxynaphthalene-3,6-disulfonic acid (53% strength) at a pH value of 6 to 7. 50 parts by weight of chrome alum were added to this solution of the azo dyestuff formed, having in the form of the free acid, the formula

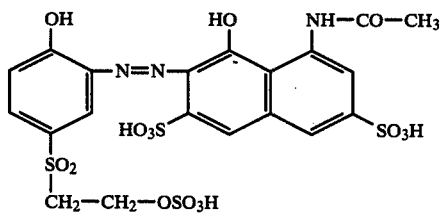

without intermediate isolation, and the mixture was adjusted to a pH of 5.3 to 5.7 with crystalline sodium acetate. The reaction mixture was then boiled under reflux for about 10 hours until no further metal-free dyestuff could be detected in the chromatogram. The solution of the 1:2 chromium complex dyestuff formed was clarified, with the addition of 10 parts by weight of kieselguhr, and thereafter spray-dried. A blue-black dyestuff powder was obtained which gave, in the presence of an agent having an alkaline action, strong, clear, navy blue prints and dyeings of very good fastness to light and wet processing on cellulose fiber materials, when fixed according to the customary and known dyeing and printing processes for reactive dyestuffs.

EXAMPLES 10 to 18

In addition, as can be seen from the tabular Examples which follow, the metal complex dyestuffs indicated in the table could be prepared from the compound of the formula (II) obtained according to the process of the invention without intermediate isolation of the diazo component itself. In fact, if the process is carried out by applying, in the general sense, the procedures indicated in Example 8 or 9 in such a way that the sulfato compounds of the formula (II) indicated in the following Examples, are first diazotized, the diazotization product is then coupled in the customary manner with the corresponding coupling component indicated in the Example, the azo compound formed is subsequently converted into the corresponding metal complex compound by treatment with a copper-, cobalt- or chromium-donating metallizing agent and the dyestuff thus obtained is isolated by evaporation or spray-drying, dyestuffs (dyestuff powders) are obtained which yield deep dyeings and prints on cotton in the color shades indicated in the Examples, which are fast to light and wet processing.

The compounds (A) and (B) stated in the Examples, represent the compounds of the following formulae

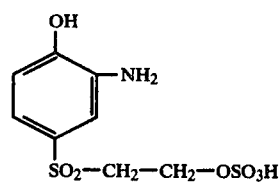
(A)

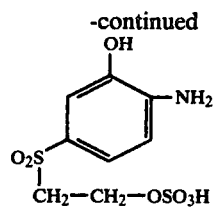
(B)

| Example | Compound of the formula II | Coupling component | Metal | Color shade on cotton |
|---|---|---|---|---|
| 10 | (A) | HO-naphthalene-2,7-disulfonic acid (6-hydroxy-naphthalene-2,7-disulfonic acid) | Copper | bluish-tinged red |
| 11 | (B) | 1-(4-sulfophenyl)-3-carboxy-5-hydroxypyrazole | Copper | yellowish-tinged brown |
| 12 | (A) | 1-hydroxy-8-acetylamino-naphthalene-3,6-disulfonic acid | Copper | red-violet |
| 13 | (A) | 2,4-dihydroxyphenyl-azo-naphthalene-4,8-disulfonic acid | Copper | brown |
| 14 | (B) | 1-hydroxy-8-acetylamino-naphthalene-3,6-disulfonic acid | Copper | violet |
| 15 | (B) | 1-hydroxy-naphthalene-4-sulfonic acid | Copper | claret |
| 16 | (A) | 1-(4-sulfophenyl)-3-methyl-5-hydroxypyrazole | Copper | yellow |
| 17 | (B) | 1-hydroxy-7-amino-naphthalene-3-sulfonic acid | Chromium | grey |

| Example | Compound of the formula II | Coupling component | Metal | Color shade on cotton |
|---|---|---|---|---|
| 18 | (A) | 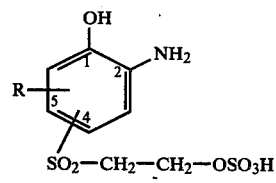 | Cobalt | black |

EXAMPLE 19

3.866 parts by weight of 6-(β-hydroxyethylsulfonyl)-benzoxazolone (94.4% pure) were initially introduced as a dry powder into a dispersion kneader. 1,607 parts by weight of 65% strength oleum were allowed to run in during a period of 20 minutes, while the machine was running. The reaction temperature was kept at 100° C. for a reaction time of 90 minutes. After cooling, 5,400 parts by weight of a product were obtained, which contained 88% of the compound of the formula

which compound had been obtained with a degree of esterification of 98%.

2.0 parts by weight of the kneaded mix thus obtained were stirred, at 0° to 5° C., into a mixture of 16 parts by volume of water and 4 parts by weight of ice, while simultaneously adding about 0.7 part by weight of sodium carbonate in portions. The pH value of the aqueous solution thus obtained was 5–5.5; the solution was clarified by filtration and evaporated to dryness in vacuo at 60° to 65° C. After grinding, 2.1 parts by weight of a yellowish white powder were obtained which contained, in addition to 8% by weight of sodium sulfate, the pure compound of the formula

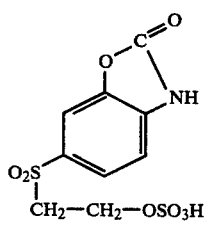

in the form of its sodium salt.

What is claimed is:

1. In a process for the preparation of an aminophenol-sulfuric acid semi-ester of the formula $$\underset{SO_2-CH_2-CH_2-OSO_3H}{\overset{OH\quad NH_2}{\text{R}}}$$

in which R is hydrogen, lower alkyl, nitro, chlorine or bromine, and the β-sulfatoethyl sulfonyl group is in the 4-position or 5-position of the benzene nucleus, by reaction comprising esterification by sulfuric acid, sulfur trioxide or sulfuric acid containing sulfur trioxide, and hydrolytic ring cleavage of a benzoxazolone compound of the formula $$\underset{SO_2-CH_2-CH_2-OH}{\text{R}}\overset{C=O}{\underset{NH}{\bigcirc}}$$

in which the β-hydroxyethylsulfonyl group is in the 5-position or 6-position of the benzoxazolone ring and R is defined as above, the improvement which comprises reacting with 1- to 2-times the equimolar amount, calculated on SO₃, of an esterifying agent selected from the group consisting of a 92 to 100% strength sulfuric acid, of sulfur trioxide and of sulfuric acid containing sulfur trioxide, optionally with the subsequent addition of water, at a temperature of from 100° to 180° C. while kneading.

2. A process as defined in claim 1, wherein the reaction is with 1.1 to 1.5 times the equimolar amount, calculated on SO₃, of said esterifying agent.

3. A process as defined in claim 1 or 2, wherein the reaction is carried out at a temperature of from 120° to 160° C.

4. A process as defined in claim 1 or 2, wherein the reaction is carried out in a machine operating with a kneading action.

5. A process as defined in claim 4, wherein the reaction is carried out in a machine operating with a continuous kneading action.

* * * * *